(12) United States Patent
Yokhin

(10) Patent No.: US 7,035,375 B2
(45) Date of Patent: Apr. 25, 2006

(54) X-RAY SCATTERING WITH A POLYCHROMATIC SOURCE

(75) Inventor: Boris Yokhin, Nazareth Illit (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 232 days.

(21) Appl. No.: 10/702,413

(22) Filed: Nov. 5, 2003

(65) Prior Publication Data

US 2005/0094766 A1    May 5, 2005

(51) Int. Cl.
    *G01N 23/201* (2006.01)
(52) U.S. Cl. .................................. 378/86; 378/89
(58) Field of Classification Search .................. 378/70, 378/86, 87, 88, 89, 143, 144
    See application file for complete search history.

(56) References Cited

U.S. PATENT DOCUMENTS

| | | | |
|---|---|---|---|
| 4,725,963 A | 2/1988 | Taylor et al. ................. 702/40 |
| 4,989,226 A | 1/1991 | Woodbury et al. ........... 378/145 |
| 5,151,588 A | 9/1992 | Kiri et al. ................. 250/208.1 |
| 5,574,284 A | 11/1996 | Farr ....................... 250/370.06 |
| 5,619,548 A | 4/1997 | Koppel ........................ 378/70 |
| 5,740,226 A | 4/1998 | Komiya et al. ................ 378/70 |
| 5,923,720 A | 7/1999 | Barton et al. ................. 378/84 |
| 6,005,915 A * | 12/1999 | Hossain et al. ............... 378/86 |
| 6,381,303 B1 | 4/2002 | Vu et al. ...................... 378/46 |
| 6,389,102 B1 | 5/2002 | Mazor et al. ................. 378/89 |
| 6,453,006 B1 | 9/2002 | Koppel et al. ................ 378/86 |
| 6,507,634 B1 | 1/2003 | Koppel et al. ................ 378/54 |
| 6,512,814 B1 | 1/2003 | Yokhin et al. ................ 378/82 |
| 6,643,354 B1 | 11/2003 | Koppel et al. ................ 378/86 |
| 6,711,232 B1 * | 3/2004 | Janik ........................... 378/70 |
| 6,744,950 B1 | 6/2004 | Aleksoff ...................... 385/48 |
| 2001/0028699 A1 | 10/2001 | Iwasaki ....................... 378/84 |
| 2001/0043668 A1 | 11/2001 | Hayashi et al. ............... 378/89 |
| 2002/0097837 A1 | 7/2002 | Fanton et al. ................ 378/82 |
| 2002/0110218 A1 | 8/2002 | Koppel et al. ................ 378/86 |
| 2004/0052330 A1 | 3/2004 | Koppel et al. ................ 378/46 |

OTHER PUBLICATIONS

Chihab et al., "New Apparatus for Grazing X-Ray Reflectometry in the Angle-Resolved Dispersive Mode", Journal of Applied Crystallography 22 (1989), p. 460.

XTF5011 Tube, Produced by Oxford Instruments of Scotts Valley, California. Jun. 1999.

Doubly-Bent Focusing Crystal Optic, Produced by XOS Inc., of Albany, New York. Jul. 2000.

(Continued)

*Primary Examiner*—David V. Bruce
*Assistant Examiner*—Courtney Thomas
(74) *Attorney, Agent, or Firm*—Morgan & Finnegan, LLP

(57) ABSTRACT

A method for inspection of a sample includes irradiating the sample with a polychromatic beam of X-rays, comprising X-ray photons having a range of respective photon energies. The X-rays scattered from the sample are received at a plurality of scattering angles using one or more sensors, which generate output signals indicative of the respective photon energies of the X-rays photons that are incident thereon. The output signals are analyzed based on the photon energies so as to determine a scattering profile of the sample at a selected photon energy within the range.

50 Claims, 4 Drawing Sheets

OTHER PUBLICATIONS

Wiener et al., "Characterization of Titanium Nitride Layers by Grazing-Emission X-Ray Fluorescence Spectrometry", in Applied Surface Science 125 (1998), p. 129.

Model S7032-0908N array, Produced by Hamamatsu, of Hamamatsu City, Japan. May 2000.

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976).

Wormington, Characterization of Pore Size Distribution in Low k Dielectrics Using X-ray Reflectivity, presented at the Sematech Gate Stack Engineering Workshop (Austin, Texas, May 2, 2002).

Ito, "X-ray Scattering Method for Determining Pore-Size Distribution in Low-k Thin Films", Presented at the International Sematech Ultra-Low-k Workshop (San Francisco, CA, Jun. 6-7, 2002).

N. Wu, et al, "Substepping and its Application to HST Imaging", Jul. 28, 2003.

Holy et al., "High Resolution X-ray Scattering from Thin Films and Multilayers", Springer Verlag 1999, pp. 18-21.

* cited by examiner

X-RAY SCATTERING WITH A POLYCHROMATIC SOURCE

FIELD OF THE INVENTION

The present invention relates generally to analytical instruments, and specifically to instruments and methods for analysis of surface layers of a sample using X-rays.

BACKGROUND OF THE INVENTION

Small-angle X-ray scattering (SAXRS) is a well-known method for surface layer characterization. It is described, for example, by Parrill et al., in "GISAXS—Glancing Incidence Small Angle X-ray Scattering," *Journal de Physique IV* 3 (December, 1993), pages 411–417, which is incorporated herein by reference. In this method, an incident X-ray beam is totally externally reflected from a surface. The evanescent wave within the surface region is scattered by microscopic structures within the region. Measurement of the scattered evanescent wave can provide information about these structures. For example, Parrill et al. describe the use of this technique for determining size information regarding islands associated with film growth on the surface.

SAXRS can be used in this manner to determine characteristics of pores in a surface layer of a low-k dielectric material formed on a silicon wafer. Nano-porous silicates and polymers are considered to be attractive materials for use in microelectronic devices with sub-0.25 µm technology, but non-destructive characterization of pore size and density has so far proved to be a difficult task. The use of diffuse X-ray reflectivity in characterizing porous low-k materials is described, for example, by Wormington in "Characterization of Pore Size Distribution in Low k Dielectrics Using X-ray Reflectivity," presented at the Sematech Gate Stack Engineering Workshop (Austin, Tex., May 2, 2002), which is incorporated herein by reference. A similar method is described by Ito in "X-ray Scattering Method for Determining Pore-Size Distribution in Low-k Thin Films," presented at the International Sematech Ultra Low-k Workshop (San Francisco, Calif., Jun. 6–7, 2002), which is also incorporated herein by reference.

Known techniques for SAXRS use a monochromatic, collimated beam of X-rays to irradiate the surface of the sample. X-ray collimators and monochromators that are known in the art tend to be very inefficient. Therefore, the flux of the monochromatic, collimated X-ray beam on the surface of the sample is generally very weak, leading to poor signal/noise ratio and low throughput in the scattering measurements. A number of attempts have been made to increase the useful X-ray flux for scattering measurements. For example, Iwasaki describes an X-ray optical device and multilayer mirror for use in a small angle scattering system in U.S. Patent Application Publication U.S. 2001/0028699 A1, whose disclosure is incorporated herein by reference. The multilayer mirror has elliptical reflection faces, which have two focal points. Thus, an X-ray beam from a source at one of the focal points is focused to a spot at the other focal point in a manner that is said to provide high precision in small-angle scattering measurements.

SUMMARY OF THE INVENTION

Embodiments of the present invention provide methods and systems for X-ray scattering analysis with enhanced sensitivity and throughput. In these embodiments, a sample is irradiated with a polychromatic beam of X-rays, so that X-rays of multiple different photon energies are scattered from the sample simultaneously. An X-ray sensor, such as a solid-state detector array, senses the scattered photons over a range of angles. The output signal of the sensor is processed, typically using an energy-dispersive technique, in order to resolve the energies of the photons that are incident on the sensor at each angle in the range. In this manner, the X-ray scattering profile of the sample can be determined as a function of angle at a single photon energy within the polychromatic envelope, or at two or more photon energies simultaneously.

The present invention thus eliminates the need to monochromatize the X-ray beam that is used in scattering measurements, so that the loss of beam flux that is usually associated with the monochromator is avoided. Furthermore, the ability provided by the present invention to determine X-ray scattering profiles at multiple energies simultaneously can be used to derive a more complete and precise picture of the properties of the sample than is generally provided by a single-energy scattering profile. The present invention is particularly useful in small-angle X-ray scattering (SAXRS) measurements, but it may also be applied to other types of X-ray scattering techniques.

There is therefore provided, in accordance with an embodiment of the present invention, a method for inspection of a sample, including:

irradiating the sample with a polychromatic beam of X-rays, including X-ray photons having a range of respective photon energies;

receiving the X-rays scattered from the sample at a plurality of scattering angles using one or more sensors, which generate output signals indicative of the respective photon energies of the X-rays photons that are incident thereon; and analyzing the output signals based on the photon energies so as to determine a scattering profile of the sample at a selected photon energy within the range.

Typically, irradiating the sample includes collimating the beam of X-rays.

In one embodiment, analyzing the output signals includes determining the scattering profile at selected, first and second photon energies within the range. Typically, irradiating the sample includes generating the beam using an X-ray tube having an anode including an anode material, wherein the first and second photon energies correspond to first and second atomic emission lines of the anode material. The anode material may include first and second elements, which generate the first and second atomic emission lines, respectively.

In some embodiments, receiving the X-rays includes receiving the scattered X-rays using an array of detector elements, arranged so that each of the elements receives the scattered X-rays at one of the plurality of scattering angles. Typically, analyzing the output signals includes counting X-ray photons that are incident on the detector elements at the selected photon energy. In one embodiment, counting the X-ray photons includes reading out a charge generated in each of the detector elements due to the scattered X-rays that are incident thereon using a readout circuit that is common to a multiplicity of the detector elements. In another embodiment, counting the X-ray photons includes processing pulses that are generated by each of the detector elements due to the scattered X-rays that are incident thereon. Optionally, the method includes receiving the X-rays reflected from the sample over multiple elevation angles using the array of detector elements, and analyzing the output signals based on the photon energies so as to determine a reflectometric profile of the sample at the selected photon energy.

Typically, analyzing the output signals includes determining the scattering profile as a function of azimuthal angle in a plane of a surface of the sample. In one embodiment, analyzing the output signals includes determining the scattering profile due to a porous surface layer that overlies a substrate of the sample, and estimating, based on the scattering profile, one or more characteristics of pores located within the porous surface layer. Typically, the sample includes a semiconductor wafer, and analyzing the output signals includes determining the scattering profile due to a thin film layer on the wafer.

There is also provided, in accordance with an embodiment of the present invention, a method for inspection of a sample, including:

irradiating the sample with a polychromatic beam of X-rays, including at least first X-rays and second X-rays having distinct, respective first and second photon energies;

detecting the first and second X-rays scattered from the sample at a plurality of scattering angles; and analyzing the detected X-rays so as to determine a scattering profile of the sample at the first and second photon energies.

In a disclosed embodiment, analyzing the detected X-rays includes determining the scattering profile as a function of azimuthal angle in a plane of a surface of the sample, wherein estimating the one or more characteristics includes determining the one or more characteristics so as to fit the scattering profile at both the first energy and the second energy.

There is additionally provided, in accordance with an embodiment of the present invention, apparatus for inspection of a sample, including:

a radiation source, which is adapted to irradiate an area on a surface of the sample with a polychromatic beam of X-rays, including at least first X-rays and second X-rays having distinct, respective first and second photon energies;

an array of detector elements arranged to receive the first and second X-rays scattered from the sample at a plurality of scattering angles, and to generate a signal responsively to the received radiation; and a signal processor, which is coupled to process the signal from the detector elements so as to determine a scattering profile of the sample at the first and second photon energies.

There is further provided, in accordance with an embodiment of the present invention, apparatus for inspection of a sample, including:

a radiation source, which is adapted to irradiate an area on a surface of the sample with a polychromatic beam of X-rays, including X-ray photons having a range of respective photon energies;

an array of detector elements arranged to receive the X-rays scattered from the sample at a plurality of scattering angles, and to generate output signals indicative of the respective photon energies of the X-ray photons that are incident thereon; and a signal processor, which is coupled to process the output signals so as to determine a scattering profile of the sample at a selected photon energy within the range.

There is moreover provided, in accordance with an embodiment of the present invention, a cluster tool for producing microelectronic devices, including:

a deposition station, which is adapted to deposit a thin-film layer on a surface of a semiconductor wafer;

an inspection station, including:

a radiation source, which is adapted to irradiate an area on a surface of the wafer with a polychromatic beam of X-rays, including at least first X-rays and second X-rays having distinct, respective first and second photon energies;

an array of detector elements arranged to receive the first and second X-rays scattered from the wafer at a plurality of scattering angles, and to generate a signal responsively to the received radiation; and a signal processor, a signal processor, which is coupled to process the signal from the detector elements in order to determine a scattering profile of the wafer at the first and second photon energies, so as to assess a quality of the thin-film layer deposited by the deposition station.

There is furthermore provided, in accordance with an embodiment of the present invention, a cluster tool for producing microelectronic devices, including:

a deposition station, which is adapted to deposit a thin-film layer on a surface of a semiconductor wafer;

an inspection station, including:

a radiation source, which is adapted to irradiate an area on a surface of the wafer with a polychromatic beam of X-rays, including X-ray photons having a range of respective photon energies;

an array of detector elements arranged to receive the X-rays scattered from the wafer at a plurality of scattering angles, and to generate output signals indicative of the respective photon energies of the X-ray photons that are incident thereon; and a signal processor, which is coupled to process the output signals in order to determine a scattering profile of the wafer at a selected photon energy within the range, so as to assess a quality of the thin-film layer deposited by the deposition station.

There is also provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

a radiation source, which is adapted to irradiate an area on a surface of the wafer with a polychromatic beam of X-rays, including at least first X-rays and second X-rays having distinct, respective first and second photon energies;

an array of detector elements arranged to receive the first and second X-rays scattered from the wafer at a plurality of scattering angles, and to generate a signal responsively to the received radiation; and a signal processor, which is coupled to process the signal from the detector elements in order Lo determine a scattering profile of the wafer at the first and second photon energies, so as to assess a quality of the thin-film layer deposited by the deposition device.

There is additionally provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

a radiation source, which is adapted to irradiate an area on a surface of the wafer with a polychromatic beam of X-rays, including X-ray photons having a range of respective photon energies;

an array of detector elements arranged to receive the X-rays scattered from the wafer at a plurality of scattering angles, and to generate output signals indicative of the respective photon energies of the X-ray photons that are incident thereon; and a signal processor, which is coupled to process the output signals in order to determine a scattering profile of the wafer at a selected photon energy within the range, so as to assess a quality of the thin-film layer deposited by the deposition device.

The present invention will be more fully understood from the following detailed description of the embodiments thereof, taken together with the drawings in which:

DETAILED DESCRIPTION OF EMBODIMENTS

Figure 1:
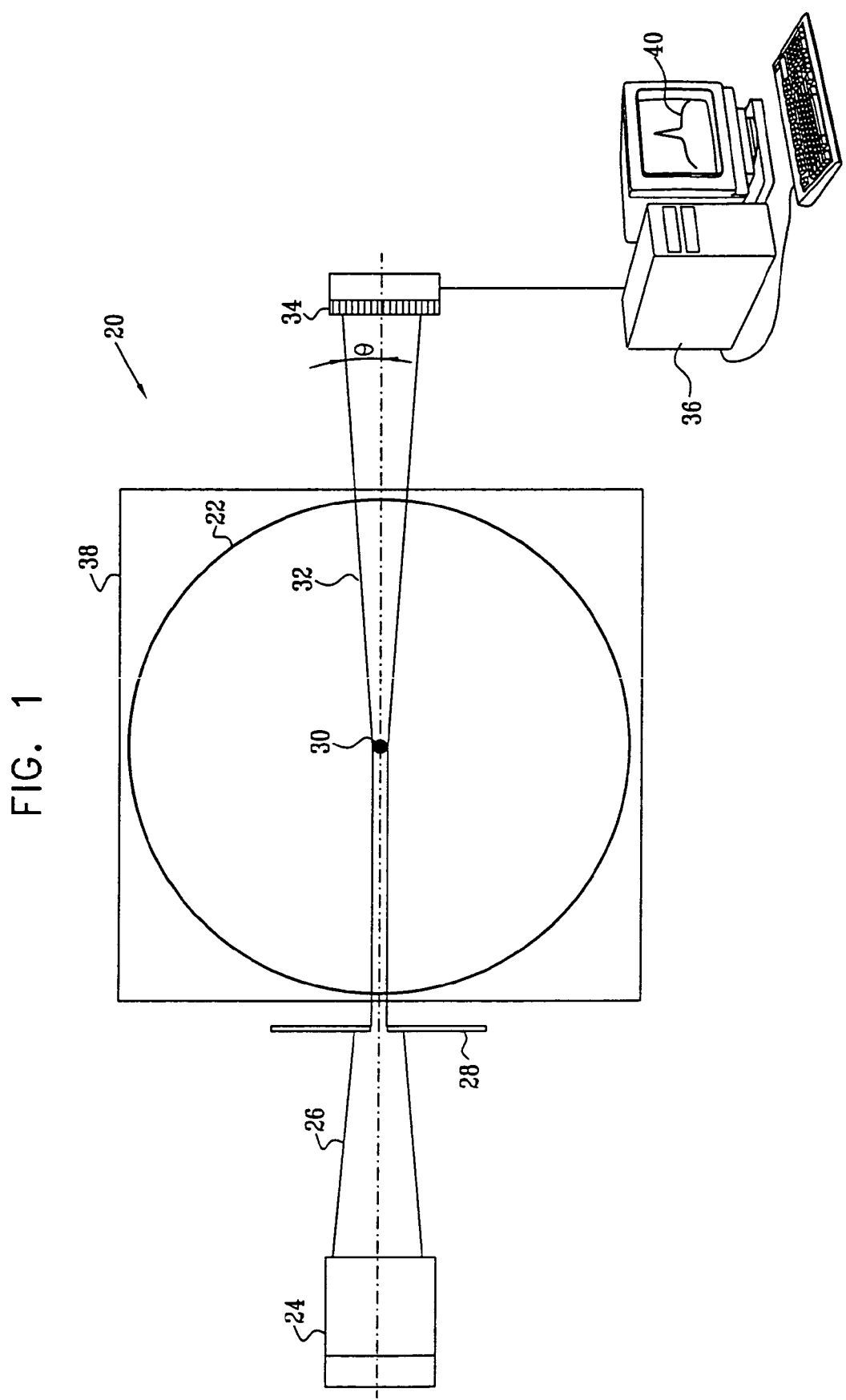
FIG. 1 is a schematic top view of a system for X-ray scattering measurement, in accordance with an embodiment of the present invention.

FIG. 1 is a schematic top view of a system 20 for small-angle scattering (SAXRS) measurements, in accordance with an embodiment of the present invention. System 20 has some features in common with a system for combined X-ray reflectometry (XRR) and SAXRS measurements that is described in U.S. patent application Ser. No. 10/364,883, filed Feb. 12, 2003, which is assigned to the assignee of the present patent application, and whose disclosure is incorporated herein by reference. Based on the XRR-related features of that system, it is possible to add XRR capability to system 20, as well, if desired.

A sample, such as a semiconductor wafer 22, for evaluation by system 20 is mounted on a motion stage 38, allowing accurate adjustment of the position and orientation of the wafer. An X-ray source 24, typically an X-ray tube with suitable focusing optics (not shown), irradiates a small area 28 on wafer 22. The X-ray source emits a polychromatic beam of X-rays, as is typical of conventional X-ray tubes known in the art. For example, an X-ray tube with a copper anode emits X-rays simultaneously on the strong copper K$\alpha$ line (8.05 keV) and on a weaker broadband continuum. Alternatively, the X-ray source may be configured so that polychromatic beam comprises at least two strong emission lines with distinct energies. For example, an X-ray tube with a tungsten anode may be used to generate X-rays on the tungsten L$\alpha$ and L$\beta$ lines at 8.4 and 9.7 keV, respectively. As another alternative, the X-ray tube may comprise a composite anode, comprising two different materials, so as to generate X-rays on spectral lines of both materials. For example, a chromium/tungsten anode can be used to generate X-rays at 5.4 keV (Cr) and 8.4 keV (W). Any suitable X-ray tube, with the proper anode type, may be used to generate the polychromatic beam. For instance, the XTF5011 X-ray tube, produced by Oxford Instruments (Scotts Valley, Calif.), may be used for this purpose.

The X-ray focusing optics of source 24 typically focus the output of the X-ray tube into a converging beam 26. For this purpose, the optics may comprise, for example, a multi-capillary array, as described in U.S. Pat. No. 6,381,303, whose disclosure is incorporated herein by reference. Alternatively, a focusing mirror may be used, for example, an elliptical mirror, such as those produced by Osmic Inc. (Troy, Mich.). A knife edge and/or a shutter (not shown) may be used to limit the angular extent of incident beam 26 in the vertical direction (i.e., perpendicular to the plane of wafer 22), while a slit 28 is used to limit the beam horizontally. The slit, knife edge and shutter are adjusted so as to collimate beam 26, typically to within an angular spread of 0.2° in each of the horizontal and vertical directions. The beam thus collimated is incident on wafer 22 at a spot 30, which is typically about 1 mm across, with an incidence angle below the critical angle for total external reflection of the wafer. The slit, knife edge and shutter and their use in controlling the X-ray beam are described in greater detail in the above-mentioned U.S. patent application Ser. No. 10/364,883. Alternatively, other X-ray optical elements, as are known in the art, may be used to collimate the incident X-ray beam, and the beam may have a larger or smaller angular spread and dimensions than the figures given above.

A scattered beam 32 of X-rays from wafer 22 is incident on a detector array 34, such as a CCD array, as described further hereinbelow. Typically, for SAXRS, array 34 collects scattered X-rays over a range of about 4° in the horizontal (azimuth–$\theta$) direction. (For clarity of illustration, the angles shown in the figure are exaggerated.) Each detector element in the array subtends a different, respective azimuthal range. Although for the sake of simplicity, only a single row of detectors elements is shown in the figure, containing a relatively small number of detector elements, array 34 generally includes a greater number of elements, arranged as either a linear array or a matrix (two-dimensional) array. Further details of the design and operation of array 34 are described in U.S. patent application Ser. No. 10/364,883. Aspects of mounting and housing the array are described in U.S. Pat. No. 6,512,814, whose disclosure is incorporated herein by reference.

In an exemplary embodiment, array 34 comprises a matrix array, such as the model S7032-1008 array produced by Hamamatsu, of Hamamatsu City, Japan. This latter array comprises 1044×256 pixels, with an overall size of 25.4×6 mm. It is capable of being operated in a line-binning mode, using special hardware supplied for this purpose by Hamamatsu, so that multiple detector elements in each row of the array function effectively as a single element with high aspect ratio. In this case, although array 34 physically comprises a two-dimensional matrix of detector elements, functionally the array takes the form of a single line of detector elements.

Alternatively, array 34 may comprise an array of PIN diodes with suitable readout circuits, possibly including integrated processing electronics, as described in U.S. Pat. No. 6,389,102, whose disclosure is incorporated herein by reference. This patent also describes alternative features of the array, including various geometrical configurations of the array (both one- and two-dimensional) and masking that may be applied to enhance the array's detection properties. These features are applicable to array 34 of the present patent application, as well. In any event, it will be understood that these various detector types are described here by way of example, and detectors of any suitable type, dimension and number can be used.

A signal processor 36 analyzes the output of array 34, so as to determine a distribution 40 of the flux of X-ray photons scattered from wafer 22 as a function of angle at a given energy or at multiple different energies. The analysis is based on determining the energy of each X-ray photon that is incident on an element of array 34, using energy-dispersive detection. When an X-ray photon strikes one of the detector elements, the number of photoelectrons that are generated in the detector element is indicative of the energy of the incident photon. The amplitude of the charge signal read out of each element of the array is, in turn, proportional to the number of photoelectrons generated by X-ray incidence, after accounting for the effects of noise and other background effects.

In many X-ray scattering applications, such as SAXRS, even with the relatively high power of incident beam 26 in system 20, the flux of scattered X-rays from wafer 22 is still very low. Therefore, in each read-out cycle of array 34, no more than a single X-ray photon is typically incident on any given detector element, other than the detector elements near $\theta=0°$, which receive a large flux of unscattered X-ray photons directly from source 24. By analyzing the amplitude of the charge signal output from each element of array 34 during each read-out cycle, processor 36 is able to determine whether the number of X-ray photons incident on the element during the cycle was zero, one or more than one. If the number of incident photons was one, processor 36 determines the energy of the X-ray photon based on the charge signal amplitude. (If the number of photons was greater than one, the signal is generally disregarded.) This procedure is repeated over many read-out cycles, and the processor counts the number of photons of each energy that are incident on each detector element during the procedure.

The reference in the paragraph above to "readout cycles" implies that a common readout and signal processing circuit is used for multiple detector elements in array 34. This arrangement is characteristic of CCD arrays, for example. Similar photon flux constraints apply when each detector in array 34 has its own readout circuit, as described in the above-mentioned U.S. Pat. No. 6,389,102, for instance. In this latter case, however, pulse processing techniques may be used to determine the energy of each incident photon. It is also possible to control the sensitivity and throughput of each detector channel by adjusting the gain and time constant that are used in the pulse processing. Energy-dispersive photon counting techniques that may be used in this context are further described in the above-mentioned U.S. Pat. No. 6,389,102.

In a typical SAXRS application, wafer 22 has one or more thin surface layers, such as thin films, at spot 30. The distribution of the scattered X-rays as a function of azimuth is indicative of microstructure, such as pores, in the surface layer of wafer 22. Processor 36 analyzes characteristics of the angular distribution in order to determine characteristics of one or more of the surface layers of the wafer, such as the thickness, density, surface quality and pore size of the layer, using methods of analysis described hereinbelow.

Figure 2:
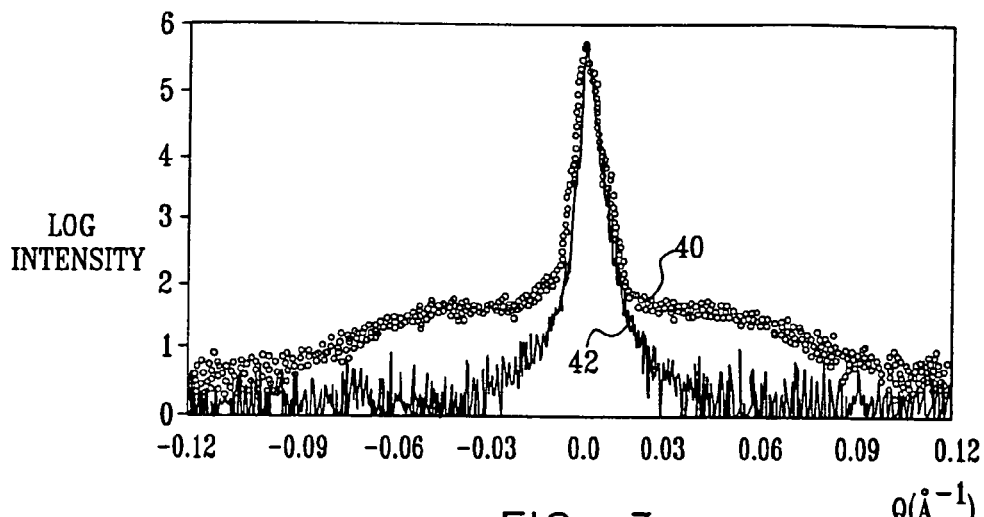
FIG. 2 is a schematic plot of X-ray scattering measured as a function of azimuthal angle for a bare silicon wafer and for a wafer covered by a porous dielectric layer, in accordance with an embodiment of the present invention.

FIG. 2 is a schematic plot of SAXRS measurement results obtained using system 20 in the above-described manner, in accordance with an embodiment of the present invention. The results are displayed as a function of the momentum transfer parameter Q, as is common in the art of X-ray scattering measurement. ($Q=4\pi \sin \theta/\lambda$, in units of inverse Angstroms, wherein $\theta$ is the azimuth and $\lambda$ is the X-ray wavelength, which was 1.54 Å in the present example.) Two measurements are shown in FIG. 2: an upper curve 40, showing measurement of scatter as a function of Q from a wafer with a porous, low-k upper dielectric layer; and a lower curve 42, showing the scatter from a bare silicon wafer. Curve 40 is normalized according to curve 42, i.e., the amplitude of the entire curve is adjusted so that the central peaks in both curves have equal heights. The effect of scattering from pores in the low-k layer can be appreciated in the elevation of curve 40, relative to curve 42, in the range between about 0.02 Å$^{-1}$ and 0.12 Å$^{-1}$.

The results shown in FIG. 2 are actually a composite of two different measurement modes: In the central range, near $\theta=0°$ (roughly $-0.02<Q<0.02$), the total charge amplitude at each element of array 34 is measured, without energy discrimination. Because of the strong contribution of direct, unscattered radiation, energy-dispersive measurement of the scattering in this range is impractical. Therefore, the signals in the central range are used only for the purpose of determining the appropriate normalization factor to apply. In the peripheral range, wherein $|Q|>0.02$, the data points represent photon counts at the specific energy of interest, in this case at $\lambda=1.54$ Å. Photon counts at other energies (due to continuum emission by source 24, or emission on other X-ray lines, for example) are disregarded in generating curve 40. The photon counts in the peripheral range at the specific energy of interest are normalized by the normalization factor determined in the central range.

Figure 3:
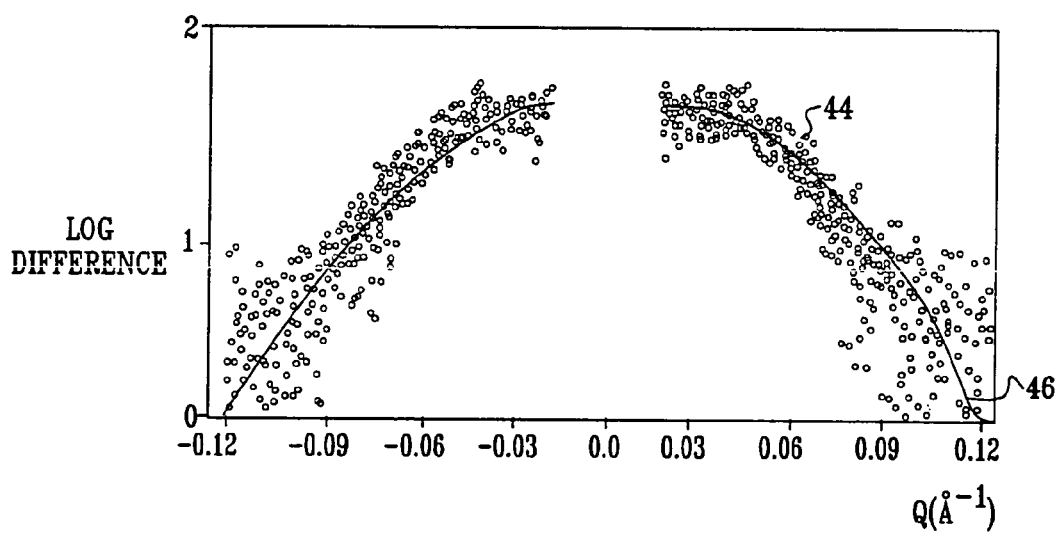
FIG. 3 is a schematic plot showing the difference between the scattering measurements of FIG. 2 and a fit of the difference to a parametric curve, in accordance with an embodiment of the present invention.

FIG. 3 is a schematic plot showing the net SAXRS signal provided by the measurements of FIG. 2. Data points 44 correspond to the measured difference between curves 40 and 42 at each value of $\theta$. A curve 46 shows a parametric fit to data points 44. The parameters of the fit include the density of the pores C, the average size of the pores $R_0$, and the width of the pore size distribution about the average, $\sigma$. An exemplary method for fitting curve 46 is described in the above-mentioned U.S. patent application Ser. No. 10/364, 883. This method of signal subtraction and curve fitting may be applied to the scattering amplitude as a function of angle that is determined by processor 36 at a single photon energy, or at two or more different photon energies.

Figure 4:
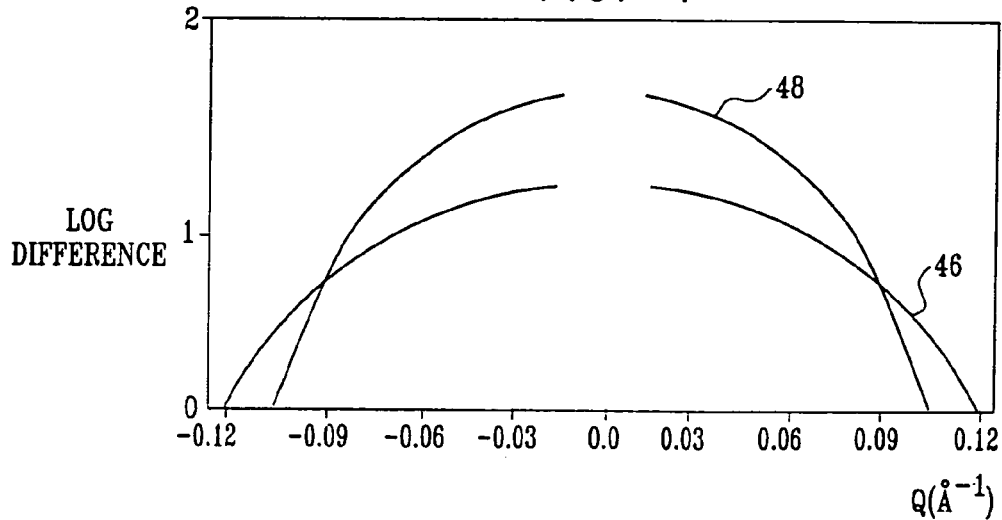
FIG. 4 is a schematic plot showing parametric curves that have been fit to X-ray scattering measurement results at two different energies, in accordance with an embodiment of the present invention.

FIG. 4 is a schematic plot showing parametric scattering curve 46, determined as described above at one photon energy, and another parametric scattering curve 48, determined at a different photon energy, in accordance with an embodiment of the present invention. The scattering results to which curves 46 and 48 are fitted are determined at both photon energies simultaneously, as described above. Since both curves 46 and 48 typically represent scattering from the same surface layer on wafer 22, the fit parameters—C, $R_0$ and $\sigma$—should be the same for both curves. This fact may be used to fit both curves 46 and 48 simultaneously, thus improving the accuracy with which the fit parameters are determined.

As noted above, system 20 is particularly useful in the inspection of thin-film layers formed on semiconductor wafers in the course of fabricating microelectronic devices.

For this purpose, system 20 may be deployed as a standalone, off-line inspection station in a semiconductor fabrication facility. Alternatively, inspection systems based on the principles described above may be integrated with semiconductor fabrication equipment for in-line measurement and monitoring. Two examples of in-line systems of this sort are described hereinbelow. Alternative equipment configurations that integrate inspection capabilities in accordance with the principles of the present invention will be apparent to those skilled in the art, upon reading the present patent application, and are considered to be within the scope of the present invention.

Figure 5:
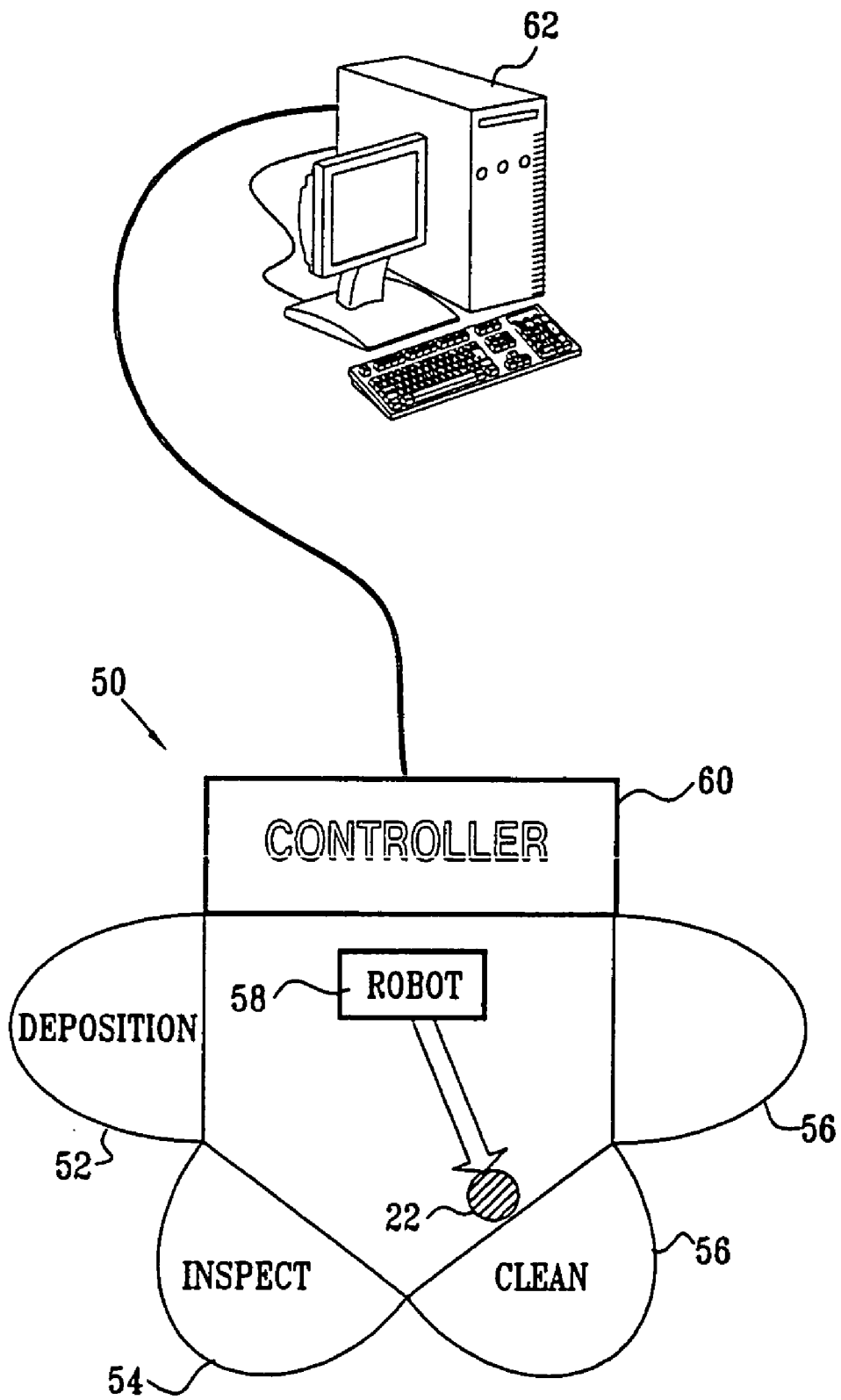
FIG. 5 is a schematic top view of a cluster tool for semiconductor device fabrication, including an inspection station in accordance with an embodiment of the present invention.

FIG. 5 is a schematic top view of a cluster tool 50 for use in semiconductor device fabrication, in accordance with an embodiment of the present invention. The cluster tool comprises multiple stations, including a deposition station 52, for depositing thin films on wafer 22, as well as an inspection station 54, and other stations 56, as are known in the art, such as a cleaning station. Inspection station 54 is constructed and operates in a manner similar to system 20, as described hereinabove. A robot 58 transfers the wafer among stations 52, 54, 56, . . . , under the control of a system controller 60. Operation of tool 50 may be controlled and monitored by an operator using a workstation 62, coupled to controller 60.

Inspection station 54 is used to perform X-ray inspection of wafers before and after selected steps in production processes carried out by deposition station 52 and other stations in tool 50. The inspection may include not only SAXRS, but also XRR. In an exemplary embodiment, deposition station 52 is used to create porous thin films, such as porous low-k dielectric layers, on the wafer, and inspection station 54 performs SAXRS evaluation, as described above. This arrangement allows early detection of process deviations and convenient adjustment and evaluation of process parameters on production wafers, using controller 60 and possibly workstation 62.

Figure 6:
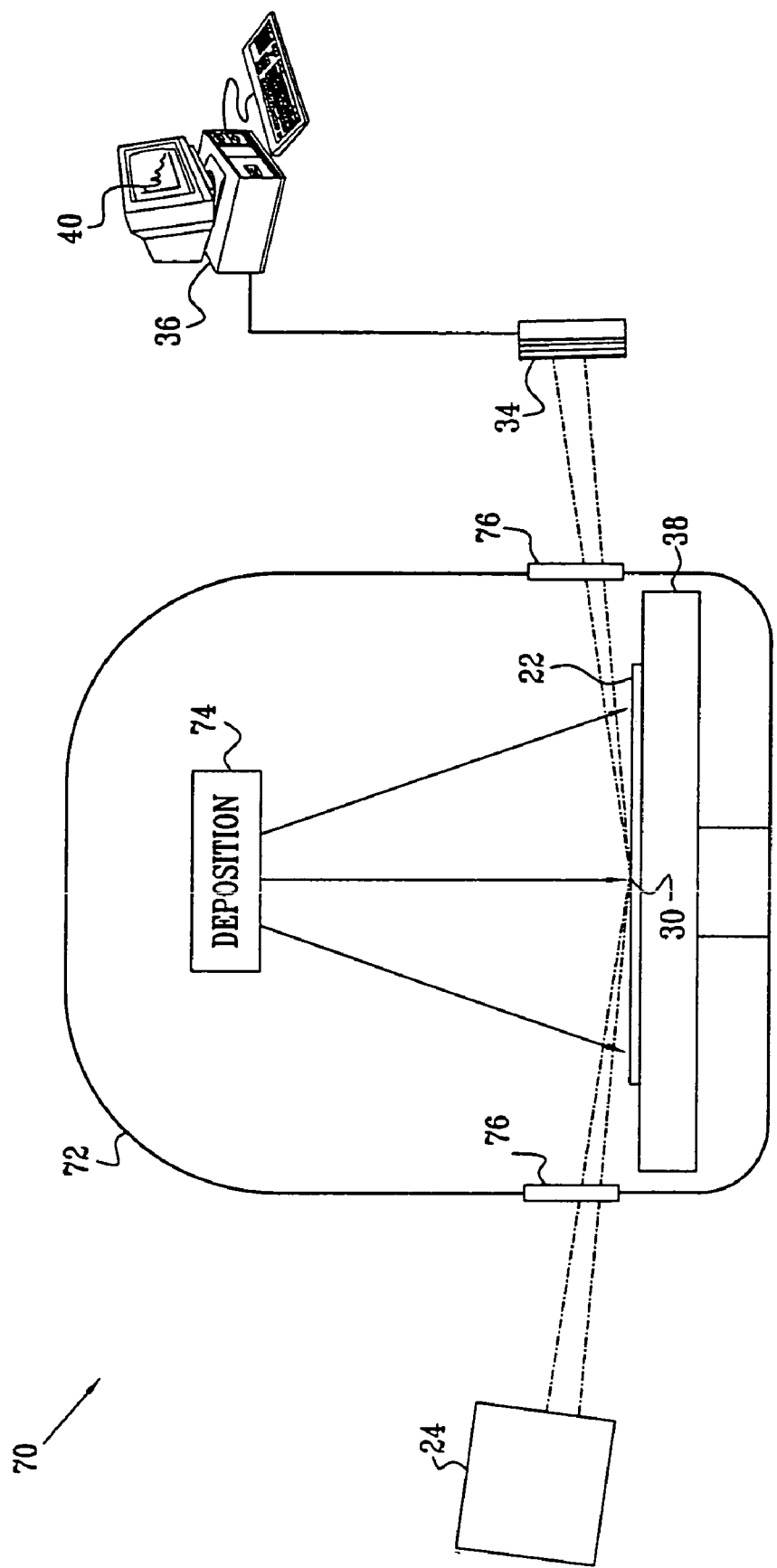
FIG. 6 is a schematic side view of a semiconductor processing chamber with X-ray inspection capability, in accordance with an embodiment of the present invention.

FIG. 6 is a schematic side view of a system 70 for semiconductor wafer fabrication and in situ inspection, in accordance with another embodiment of the present invention. System 70 comprises a vacuum chamber 72, containing deposition apparatus 74, for creating thin films on wafer 22, as is known in the art. The wafer is mounted on motion stage 38 within chamber 72. The chamber typically comprises X-ray windows 76. X-ray source 24 irradiates spot 30 on the wafer via one of windows 76, in the manner described above. The slit shown in FIG. 1 is omitted from FIG. 6 for the sake of simplicity, but typically, elements of this sort are integrated into source 24 or within chamber 72.

X-rays scattered from spot 30 are received by array 34 via another one of windows 76. Processor 36 receives signals from detector array 34, and processes the signals in order to assess characteristics of thin-film layers in production within chamber 72. The results of this assessment may be used in controlling deposition apparatus 74 so that the films produced by system 70 have desired characteristics, such as thickness, density and porosity.

Although the embodiments described above deal mainly with determining porosity characteristics of low-k dielectric layers on semiconductor wafers, the principles of the present invention can similarly be used in other X-ray scattering applications, on samples of various types, as well as in other types of radiation-based analysis, using not only X-rays, but also other ionizing radiation bands. Furthermore, a polychromatic X-ray source and a detector array with energy-dispersive signal processing may similarly be used in XRR, particularly for XRR measurements at high elevation angles, at which reflections are relatively weak. A single detector array, with suitable means for rotating the array (as described in the above-mentioned U.S. patent application Ser. No. 10/364,883) and with energy-dispersive processing, may be used in this manner to make both XRR and SAXRS measurements in a single system.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection of a sample, comprising:
   irradiating the sample with a polychromatic beam of X-rays, comprising X-ray photons having a range of respective photon energies;
   receiving the X-rays scattered from the sample at a plurality of scattering angles using one or more sensors, which generate output signals indicative of the respective photon energies of the X-rays photons that are incident thereon at each of the plurality of scattering angles; and
   analyzing the output signals based on the photon energies so as to determine a scattering profile of the sample at a selected photon energy within the range.

2. The method according to claim 1, wherein irradiating the sample comprises collimating the beam of X-rays.

3. The method according to claim 1, wherein analyzing the output signals comprises determining the scattering profile at selected, first and second photon energies within the range.

4. The method according to claim 3, wherein irradiating the sample comprises generating the beam using an X-ray tube having an anode comprising an anode material, wherein the first and second photon energies correspond to first and second atomic emission lines of the anode material.

5. The method according to claim 4, wherein the anode material comprises first and second elements, which generate the first and second atomic emission lines, respectively.

6. The method according to claim 1, wherein receiving the X-rays comprises receiving the scattered X-rays using an array of detector elements, arranged so that each of the elements receives the scattered X-rays at one of the plurality of scattering angles.

7. The method according to claim 6, wherein analyzing the output signals comprises counting X-ray photons that are incident on the detector elements at the selected photon energy.

8. The method according to claim 7, wherein counting the X-ray photons comprises reading out a charge generated in each of the detector elements due to the scattered X-rays that are incident thereon using a readout circuit that is common to a multiplicity of the detector elements.

9. The method according to claim 7, wherein counting the X-ray photons comprises processing pulses that are generated by each of the detector elements due to the scattered X-rays that are incident thereon.

10. The method according to claim 6, and comprising receiving the X-rays reflected from the sample over multiple elevation angles using the array of detector elements, and analyzing the output signals based on the photon energies so as to determine a reflectometric profile of the sample at the selected photon energy.

11. The method according to claim 1, wherein analyzing the output signals comprises determining the scattering profile as a function of azimuthal angle in a plane of a surface of the sample.

12. The method according to claim 11, wherein analyzing the output signals comprises determining the scattering profile due to a porous surface layer that overlies a substrate of the sample, and estimating, based on the scattering profile, one or more characteristics of pores located within the porous surface layer.

13. The method according to claim 1, wherein the sample comprises a semiconductor wafer, and wherein analyzing the output signals comprises determining the scattering profile due to a thin film layer on the wafer.

14. A method for inspection of a sample, comprising:
irradiating the sample with a polychromatic beam of X-rays, comprising at least first X-rays and second X-rays having distinct, respective first and second photon energies;
detecting the first and second X-rays scattered from the sample at a plurality of scattering angles; and
analyzing the detected X-rays so as to determine a scattering profile of the sample at the first and second photon energies.

15. The method according to claim 14, wherein irradiating the sample comprises collimating the beam of X-rays.

16. The method according to claim 14, wherein irradiating the sample comprises generating the beam using an X-ray tube having an anode comprising an anode material, wherein the first and second photon energies correspond to first and second atomic emission lines of the anode material.

17. The method according to claim 16, wherein the anode material comprises first and second elements, which generate the first and second atomic emission lines, respectively.

18. The method according to claim 14, wherein detecting the first and second X-rays comprises receiving the scattered X-rays using an array of detector elements, arranged so that each of the elements receives the scattered X-rays at one of the plurality of scattering angles.

19. The method according to claim 18, wherein receiving the scattered X-rays comprises generating, at each of the detector elements on which one of the X-rays is incident, a charge signal that is indicative of a photon energy of the one of the X-rays, and wherein analyzing the detected X-rays comprises determining the photon energies of the incident X-rays responsively to an amplitude of the charge signal.

20. The method according to claim 19, wherein analyzing the detected X-rays comprises counting X-ray photons that are incident on the detector elements at each of the first and second photon energies so as to determine the scattering profile at each of the photon energies.

21. The method according to claim 14, wherein analyzing the detected X-rays comprises determining the scattering profile as a function of azimuthal angle in a plane of a surface of the sample.

22. The method according to claim 21, wherein analyzing the detected X-rays comprises determining the scattering profile due to a porous surface layer that overlies a substrate of the sample, and estimating, based on the scattering profile, one or more characteristics of pores located within the porous surface layer.

23. The method according to claim 22, wherein estimating the one or more characteristics comprises determining the one or more characteristics so as to fit the scattering profile at both the first energy and the second energy.

24. The method according to claim 14, wherein the sample comprises a semiconductor wafer, and wherein analyzing the detected X-rays comprises determining the scattering profile due to a thin film layer on the wafer.

25. Apparatus for inspection of a sample, comprising:
a radiation source, which is adapted to irradiate an area on a surface of the sample with a polychromatic beam of X-rays, comprising at least first X-rays and second X-rays having distinct, respective first and second photon energies;
an array of detector elements arranged to receive the first and second X-rays scattered from the sample at a plurality of scattering angles, and to generate a signal responsively to the received radiation; and
a signal processor, which is coupled to process the signal from the detector elements so as to determine a scattering profile of the sample at the first and second photon energies.

26. The apparatus according to claim 25, wherein the radiation source comprises a collimator, which is adapted to collimate the beam of X-rays.

27. The apparatus according to claim 25, wherein the radiation source comprises an X-ray tube having an anode comprising an anode material, wherein the first and second photon energies correspond to first and second atomic emission lines of the anode material.

28. The apparatus according to claim 27, wherein the anode material comprises first and second elements, which generate the first and second atomic emission lines, respectively.

29. The apparatus according to claim 25, wherein each of thedetectorelements is adapted to generate, upon incidence of one of the X-rays thereon, a charge signal that is indicative of a photon energy of the one of the X-rays, and wherein the signal processor is adapted to determine the photon energies of the incident X-rays responsively to an amplitude of the charge signal.

30. The apparatus according to claim 29, wherein the signal processor is adapted to count X-ray photons that are incident on the detector elements at each of the first and second photon energies so as to determine the scattering profile at each of the photon energies.

31. The apparatus according to claim 25, wherein the array of detector elements has is arranged to resolve the received X-rays along an array axis parallel to a surface of the sample, and wherein the signal processor is adapted to determine the scattering profile as a function of azimuthal angle in a plane of the surface responsively to the signal from the detector elements.

32. The apparatus according to claim 31, wherein the signal processor is adapted to determine the scattering profile due to a porous surface layer that overlies a substrate of the sample, and to estimate, based on the scattering profile, one or more characteristics of pores located within the porous surface layer.

33. The apparatus according to claim 32, wherein the signal processor is adapted to estimate the one or more characteristics so as to fit the scattering profile at both the first energy and the second energy.

34. The apparatus according to claim 25, wherein the sample comprises a semiconductor wafer, and wherein the signal processor is adapted to determine the scattering profile due to a thin film layer on the wafer.

35. Apparatus for inspection of a sample, comprising:
a radiation source, which is adapted to irradiate an area on a surface of the sample with a polychromatic beam of X-rays, comprising X-ray photons having a range of respective photon energies;

an array of detector elements arranged to receive the X-rays scattered from the sample at a plurality of scattering angles, and to generate output signals indicative of the respective photon energies of the X-ray photons that are incident thereon at each of the plurality of scattering angles; and a signal processor, which is coupled to process the output signals so as to determine a scattering profile of the sample at a selected photon energy within the range.

36. The apparatus according to claim 35, wherein the radiation source comprises a collimator, which is adapted to collimate the beam of X-rays.

37. The apparatus according to claim 35, wherein the signal processor is adapted to determine the scattering profile at selected, first and second photon energies within the range.

38. The apparatus according to claim 37, wherein the radiation source comprises an X-ray tube having an anode comprising an anode material, wherein the first and second photon energies correspond to first and second atomic emission lines of the anode material.

39. The apparatus according to claim 38, wherein the anode material comprises first and second elements, which generate the first and second atomic emission lines, respectively.

40. The apparatus according to claim 35, wherein the signal processor is adapted to count X-ray photons that are incident on the detector elements at the selected photon energy.

41. The apparatus according to claim 40, wherein the array of detector elements comprises a readout circuit that is common to a multiplicity of the detector elements, and which is adapted to read out a charge generated in each of the detector elements due to the scattered X-rays that are incident thereon, and wherein the signal processor is adapted to process the charge read out by the readout circuit in order to count the X-ray photons at the selected photon energy.

42. The apparatus according to claim 40, wherein the detector elements are adapted to generate pulses responsively to the scattered X-rays that are incident thereon, and wherein the signal processor is adapted to process the pulses in order to count the X-ray photons at the selected photon energy.

43. The apparatus according to claim 35, wherein the array of detector elements is further adapted to receive the X-rays reflected from the sample over multiple elevation angles, and wherein the signal processor is further adapted to process the output signals based on the photon energies so as to determine a reflectometric profile of the sample at the selected photon energy.

44. The apparatus according to claim 35, wherein the array of detector elements has is arranged to resolve the received X-rays along an array axis parallel to a surface of the sample, and wherein the signal processor is adapted to determine the scattering profile as a function of azimuthal angle in a plane of the surface responsively to the output signals.

45. The apparatus according to claim 44, wherein the signal processor is adapted to determine the scattering profile due to a porous surface layer that overlies a substrate of the sample, and to estimate, based on the scattering profile, one or more characteristics of pores located within the porous surface layer.

46. The apparatus according to claim 35, wherein the sample comprises a semiconductor wafer, and wherein the signal processor is adapted to determine the scattering profile due to a thin film layer on the wafer.

47. A cluster tool for producing microelectronic devices, comprising:

a deposition station, which is adapted to deposit a thin-film layer on a surface of a semiconductor wafer;

an inspection station, comprising:
a radiation source, which is adapted to irradiate an area on a surface of the wafer with a polychromatic beam of X-rays, comprising at least first X-rays and second X-rays having distinct, respective first and second photon energies;

an array of detector elements arranged to receive the first and second X-rays scattered from the wafer at a plurality of scattering angles, and to generate a signal responsively to the received radiation; and a signal processor, which is coupled to process the signal from the detector elements in order to determine a scattering profile of the wafer at the first and second photon energies, so as to assess a quality of the thin-film layer deposited by the deposition station.

48. A cluster tool for producing microelectronic devices, comprising:

a deposition station, which is adapted to deposit a thin-film layer on a surface of a semiconductor wafer;

an inspection station, comprising:
a radiation source, which is adapted to irradiate an area on a surface of the wafer with a polychromatic beam of X-rays, comprising X-ray photons having a range of respective photon energies;

an array of detector elements arranged to receive the X-rays scattered from the wafer at a plurality of scattering angles, and to generate output signals indicative of the respective photon energies of the X-ray photons that are incident thereon at each of the plurality of scattering angles; and a signal processor, which is coupled to process the output signals in order to determine a scattering profile of the wafer at a selected photon energy within the range, so as to assess a quality of the thin-film layer deposited by the deposition station.

49. Apparatus for producing microelectronic devices, comprising:

a production chamber, which is adapted to receive a semiconductor wafer;

a deposition device, which is adapted to deposit a thin-film layer on a surface of the semiconductor wafer within the chamber;

a radiation source, which is adapted to irradiate an area on a surface of the wafer with a polychromatic beam of X-rays, comprising at least first X-rays and second X-rays having distinct, respective first and second photon energies;

an array of detector elements arranged to receive the first and second X-rays scattered from the wafer at a plurality of scattering angles, and to generate a signal responsively to the received radiation; and a signal processor, which is coupled to process the signal from the detector elements in order to determine a scattering profile of the wafer at the first and second photon energies, so as to assess a quality of the thin-film layer deposited by the deposition device.

50. Apparatus for producing microelectronic devices, comprising:

a production chamber, which is adapted to receive a semiconductor wafer;

a deposition device, which is adapted to deposit a thin-film layer on a surface of the semiconductor wafer within the chamber;

a radiation source, which is adapted to irradiate an area on a surface of the wafer with a polychromatic beam of X-rays, comprising X-ray photons having a range of respective photon energies;

an array of detector elements arranged to receive the X-rays scattered from the wafer at a plurality of scattering angles, and to generate output signals indicative of the respective photon energies of the X-ray photons that are incident thereon at each of the plurality of scattering angles; and a signal processor, which is coupled to process the output signals in order to determine a scattering profile of the wafer at a selected photon energy within the range, so as to assess a quality of the thin-film layer deposited by the deposition device.

* * * * *